//  
United States Patent [19]
Tanaka

[11] 4,412,624
[45] Nov. 1, 1983

[54] HANGING MEMBER FOR HANGING A CONTAINER IN AN INVERTED POSITION

[75] Inventor: Nobuyoshi Tanaka, Osaka, Japan

[73] Assignee: Takeda Chemical Industries, Ltd., Osaka, Japan

[21] Appl. No.: 364,643

[22] Filed: Apr. 2, 1982

[30] Foreign Application Priority Data

Apr. 3, 1981 [JP] Japan ............................ 56-48793[U]

[51] Int. Cl.$^3$ ............................................ B65D 25/22
[52] U.S. Cl. ................................ 215/100 A; 248/318; 294/31.2
[58] Field of Search ...................... 215/100 A, 100 R; 294/31.2; 248/318, 359; 220/94 R

[56] References Cited

U.S. PATENT DOCUMENTS

| | | | |
|---|---|---|---|
| 3,635,367 | 1/1972 | Morita et al. | 215/100 A |
| 3,653,610 | 4/1972 | Owen | 294/31.2 |
| 3,688,935 | 9/1972 | Owen et al. | 215/100 A |
| 3,717,277 | 2/1973 | Stengle, Jr. | 215/100 A |
| 3,744,658 | 7/1973 | Fujio | 215/100 A |
| 4,306,662 | 12/1981 | Sciortino | 215/100 A |

*Primary Examiner*—Donald F. Norton
*Attorney, Agent, or Firm*—Wenderoth, Lind & Ponack

[57] ABSTRACT

A hanger for hanging a container in an inverted position, and the combination of the hanger and the container. The container has a ring member on the bottom thereof with a pair of semi-circular hanger members lying along and spaced from the inner peripheral edge thereof in the plane of the ring member when in the non-use condition of the hanger. The semi-circular hanger members have the ends integrally attached to the inner peripheral edge of the ring member at substantially diametrically opposite points of the ring member. A transverse hanger member is attached to and extends between substantially the midpoints of the semi-circular hanger members transverse to a line between the points at which the semi-circular hanger members are integrally attached to the ring member, and the transverse hanger member lies in the plane of the ring member in the non-use condition of the hanger. All of the members are made of a flexible synthetic resin material, and the integral attachments of the semi-circular hanger members to the ring member and the transverse hanger member to the semi-circular hanger members are flexible and permit the members to hinge relative to each other. In use, the semi-circular hanger members are pivoted upwardly out of the plane of the ring member and the transverse hanger member is looped upwardly for hooking over a laterally extending support member or hook.

20 Claims, 8 Drawing Figures

4,412,624

HANGING MEMBER FOR HANGING A CONTAINER IN AN INVERTED POSITION

The present invention relates to a hanging member for hanging a container in an inverted position, and to a container with such a hanging member as a part thereof, and more particularly relates to a hanging member for hanging a bottle intended to be used for dripping fluids into the body of a patient in an inverted position, and to such a bottle with a hanging member thereon.

BACKGROUND OF THE INVENTION AND PRIOR ART

Bottles for dripping fluid into a patient, and which are intended to be hung in an inverted position, are well known, and many devices have been proposed for hanging these bottles in an inverted position.

One such recently proposed hanging device is as shown in U.S. Pat. Nos. 3,635,367, and 3,744,658, and this type of bottle with such a hanging device is as shown in FIG. 8. The hanging device has a ring-shaped part 20 with an opening 21 in the center thereof through which the bottom of the bottle is exposed. A bail or hanger member 23 is, when the bottle is not in use, positioned within the aperture, lying in the plane of the ring shaped part 20, an integrally attached to the inner periphery 22 of the aperture 21 by hinge portions 24. The cap member and bail are molded from a flexible synthetic plastic material, such as polyethylene, so that the bail can be pivoted away from the bottom of the container into a position in which it projects generally away from the bottom of the container by twisting the hinge portions 24. The bail is then hooked over a horizontal hanger, hook, or the like for supporting the bottle in an inverted position.

However, depending upon the type of fluid which is contained in the bottle and which is being dripped into the patient, it may be necessary to keep a constant and accurate watch on the amount of fluid which is delivered from the bottle. For certain types of vascular contrast medium, for example angio- or arteriography contrast medium, the angiography or arteriography is performed after a certain amount of the contrast medium has been infused into the patient, and again after a certain additional amount of the medium has been infused. In such cases, it is necessary to read accurately the amount of fluid which has been infused by inspecting the graduations on the sidewall of the inverted bottle. If the bottle has not been hung in a perfectly vertical position, however, the level of the fluid in the bottle cannot be accurately determined.

When such a bottle is hung by a hanger as shown in FIG. 8, the bail 23 does not always extend perfectly perpendicularly away from the plane of the bottom of the container, due to the resiliency of the plastic material of which the hanger is molded, so that the bottle tends to hang in a slightly tilted position with respect to the vertical.

OBJECTS AND BRIEF DESCRIPTION OF THE INVENTION

It is an object of the present invention to provide a hanger for a container, and particularly a bottle for dripping fluid into a patient, which is to be hung in an inverted position, and which hanger holds the bottle in a perfectly perpendicular position.

It is a further object of the invention to provide such a hanger which can be easily molded from a flexible synthetic plastic material, such as polyethylene, and which can be easily secured to the bottom of the bottle.

To this end, the present invention provides a hanger which has a ring member which is held on the bottom of the container, for example by a film of heat shrinkable material which has been heat shrunk onto the container and the edge of which overlaps the ring member, and a pair of semi-circular hanger members lying along and spaced from the inner peripheral edge of the ring member and in the plane of the ring member when the hanger is not in use, the semi-circular hanger members having the ends integrally attached to the inner peripheral edge of the ring member at substantially diametrically opposite points of the ring member. A transverse hanger member is attached to and extends between substantially the midpoints of the semi-circular hanger members transverse to a line between the points at which the semi-circular hanger members are integrally attached to the ring member, and in the plane of the ring member in the non-use condition of the hanger. All of the members are molded integrally from a bendable synthetic resin material, such as polyethylene, and the integral attachments of the semi-circular hanger member to the ring member and said transverse hanger member to the semi-circular hanger members are flexible and permit said members to hinge relative to each other. During use, the semi-circular hanger members are pivoted upwardly out of the plane of the ring member away from the bottom of the container, and the transverse hanger member is moved upwardly for hooking over a laterally extending support member or hook.

Because there ae two semi-circular hanger members which pivot upwardly toward each other, and because the transverse hanger member extending between them forms a loop above them, when the thus looped transverse hanger member is placed over the hook or support member, the container on which the hanger is mounted will hang in an inverted position perfectly vertically from the transverse hanger member.

BRIEF DESCRIPTION OF THE FIGURES

The invention will now be described in greater detail in connection with the accompanying drawings, in which.

DETAILED DESCRIPTION OF THE INVENTION

Figure 1:
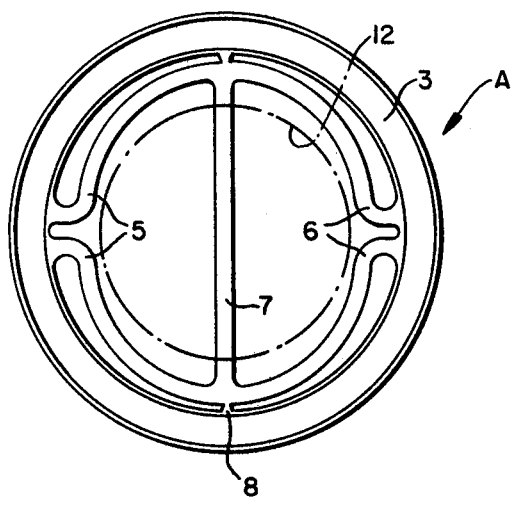
FIG. 1 is a top plan view of a hanger according to the present invention with the parts in the non-use condition.

Referring first to the embodiment of FIGS. 1-4, the hanger A of the present invention comprises a ring member 3 which, when the hanger is mounted on a container 1, lies over the bottom 2 of the container. A pair of semi-circular hanger members 5 lie along and are spaced from the inner peripheral edge of the ring member 3, and, when in the non-use condition, lie in the plane of the ring member. The ends 6 of the semi-circular hanger members 5 are integrally attached to the inner peripheral edge of the ring member 3 at substantially diametrically opposite points of the ring member.

A transverse hanger member 7 is attached to and extends between substantially the midpoints of the semi-circular hanger members 5, and extends transverse to a line between the points at which the ends 6 of the semi-circular hanger members 5 are integrally attached to the ring member 3. Again, in the non-use condition, the transverse hanger member 7 lies in the plane of the ring member 3.

All of these members are molded from a flexible or bendable synthetic resin material, such as polyethylene or polyvinyl chloride, and the integral attachments of the semi-circular hanger members 5 to the ring 3 at the ends 6, and the attachments of the transverse hanger member 7 to the semi-circular hanger members 5 are flexible, and permit these members to hinge relative to each other.

Figure 4:
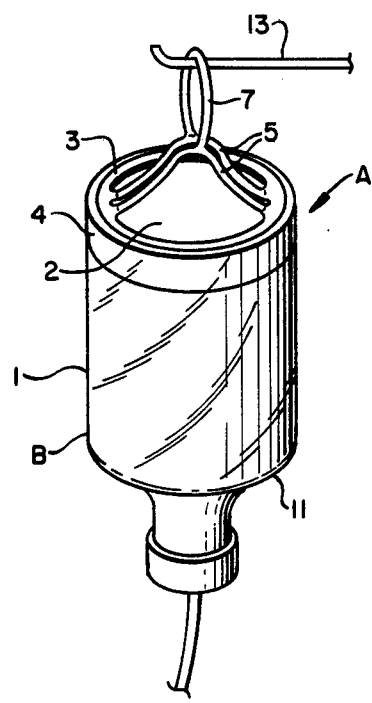
FIG. 4 is a perspective view of the hanger of the present invention on a container hung from a hanger or support.

In use, the semi-circular hanger members 5 are pivoted upwardly out of the plane of the ring member 3 away from the bottom 2 of the container A, and so that the center portions thereof approach each other, and the transverse hanger member 7 forms an upwardly extending loop between the upwardly pivoted semi-circular hanger members 5, as shown in FIG. 4. The thus looped transverse hanger member 7 is placed over a support member or hook 13 which can extend from a stand, from a wall, or the like, thus supporting the bottle 1 in an inverted position.

It will be seen that because the two semi-circular hanger members 5 pivot upwardly so that the mid portions thereof approach each other, and because the transverse hanger member 7 extends in a loop between these mid portions, when the looped transverse hanger member 7 is placed on the hook 13, the bottle 1 will be supported in an inverted and perfectly vertical position. Any forces due to the resiliency of the semi-circular hanger members 5 or the transverse hanger member 7 are equal and opposite so that they do not tend to tilt the bottle 1.

It is preferred to provide break away connectors 8 between the semi-circular hanger members 5 and the inner periphery of the ring member 3, and these are preferably provided in alignment with the transverse hanger member 7. These prevent unintentional lifting of the semi-circular hanger members 5 and the transverse hanger member 7 out of the plane of the ring member 3 during storage of the container or during its handling prior to being hung in the inverted position.

In addition, it is preferred to have a cylindrical wall portion 4 depending from the outer peripheral edge of the ring member 3 for locating the ring member 3 on the bottom of the container. The cylindrical wall portion 4 fits closely around the bottom of the peripheral wall of the bottle 1.

In addition, in order to space the ring member 3 and the transverse hanger member 7 slightly from the bottom of the container, so that they can be easily gripped when it is desired to move these members to the operative positions, projections 9 are provided on the surface of the transverse hanger member 7 which faces the bottom of the bottle, and a pair of rib members 10 are provided which depend from the inner peripheral edge of the ring member 3, preferably at the positions of the connections of the ends 6 of the semi-circular hanger members 5 to the ring member 3. These ribs act not only as spacers, but also as reinforcement for the ring member where the semi-circular hanger members are pivotably connected thereto.

Figure 5:
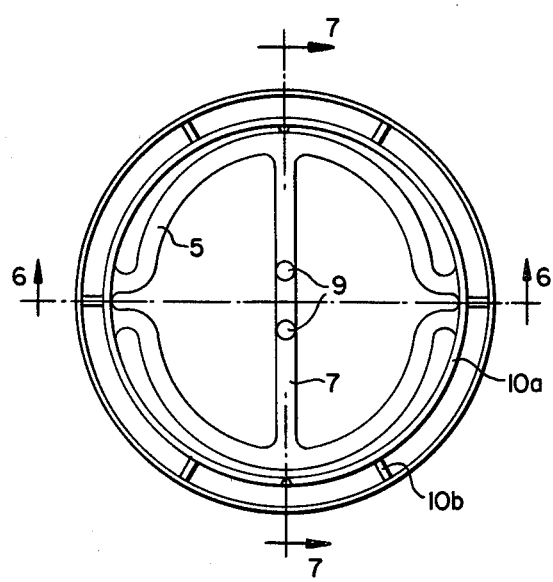
FIG. 5 is a bottom plan view of a modified form of the hanger of the present invention.
Figure 6:
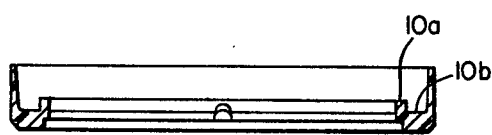
FIG. 6 is a sectional view taken along the line 6—6 of FIG. 5.
Figure 7:
FIG. 7 is a sectional view taken along the line 7—7 of FIG. 5.
Figure 8:
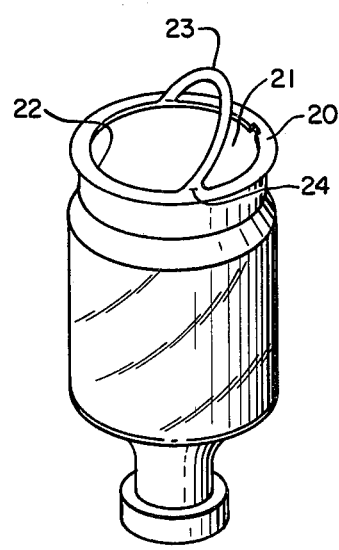
FIG. 8 is a perspective view of a prior art hanger and inverted container.

In the embodiment of FIGS. 5-7, the ribs 10 have been replaced with a continuous rib 10a which extends completely around the inner periphery of the ring 3. Radially extending ribs 10b can be provided between the rib 10a and the depending cylindrical wall portion 4 for further reinforcement of the structure of the hanger.

Figure 2:
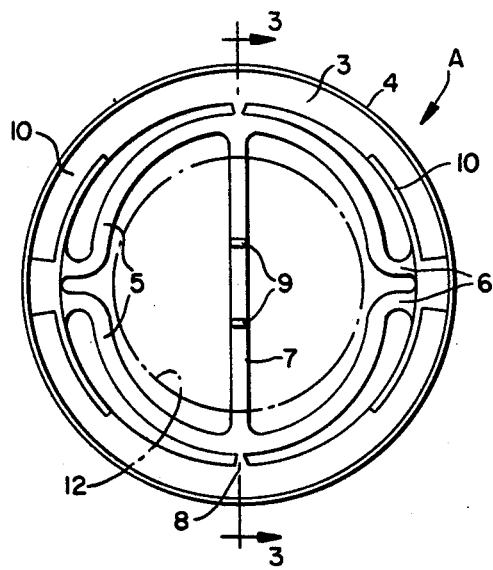
FIG. 2 is a bottom plan view of the hanger of FIG. 1.
Figure 3:
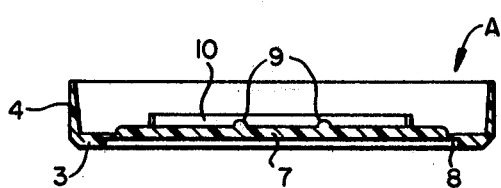
FIG. 3 is a section taken along the line 3—3 of FIG. 2.

For holding the hanger onto the bottom of the bottle 1, it is preferred to provide a film of heat shrinkable synthetic resin material B, such as polyvinyl chloride, around the outside of the container and extending over the shoulder 11 of the container, and extending around the joint between the sidewall of the container and the bottom of the container and overlapping the ring member 3. Preferably the inner periphery of the heat shrinkable film B extends inwardly over the hanger A radially inwardly of the ring 3 and the semi-circular hanger members 5 to the position of the chain line 12 as shown in FIGS. 1 and 2. With this construction, when the transverse hanger member 7 is pulled away from the bottom of the container, the semi-circular hanger members 5 are easily pulled outwardly away from the container against the action of the heat shrunk film B. The heat shrunk film A nevertheless reinforces the semi-circular hanger members 5.

The ratio of the outer diameter of the semi-circular hanger members 5 to the diameter of the edge of the aperture 12 of the heat shrunk film may be from 1:0.8 to 1:0.5, and preferably is from 1:0.7 to 1:0.5.

With this arrangement, even if the transverse hanger member 7 is released, it will not return to its original position, but will remain looped away from the bottom of the container, thus enabling it to be rehung on the hook or support 13.

It will thus be seen that there has been provided a hanger for a bottle to be held in an inverted position, and a bottle with such a hanger thereon, and in the disclosed construction, the weight of the bottle as hung from the hanger is evenly distributed and supported at the four points of the hanger, i.e. the connections of the semi-circular hanger members 5 to the ring 3, and the connections of the transverse hanger member 7 to the semi-circular hanger members 5. There is further no concentration of the load due to the weight of the bottle at only two points, as in the prior art arrangement, so that the danger of the hanging bottle tearing the connections between the parts of the hanger is substantially eliminated.

Even though the semi-circular hanger members 5 may tend to return to their non-use positions, the provision of the single transverse hanger member 7 extending transversely between the two semi-circular hanger members ensures that the bottle supported by the hanger will remain in a vertical position.

The provision of the ribs on the ring member 3 at the positions where the semi-circular hanger members are attached to the ring 3 improves the strength of the structure, and because the ribs will, when the hanger is mounted on the bottle, abut the bottom of the bottle, they help provide a clearance between the undersurface of the parts of the hanger and the bottom of the bottle so that the transverse hanger member 7 can be easily grasped with the fingers to pivot the semi-circular hanger members 5 out of the plane of the ring member 3.

Although the present invention has been fully described by way of example with reference to the accompanying drawings, it is to be noted that various changes and modifications will be apparent to those skilled in the art. Therefore, unless otherwise such changes and modifications depart from the scope of the present invention, as defined in the appended claims, they should be construed as being included therein.

What is claimed is:

1. A hanger for hanging a container in an inverted position, comprising:
   a ring member adapted to be placed on the bottom of the container;
   a pair of semi-circular hanger members lying along and spaced from the inner peripheral edge of said ring member and in the plane of said ring member in the non-use condition of said hanger, said semi-circular hanger members having the ends integrally attached to the inner peripheral edge of said ring member at substantially diametrically opposite points of said ring member; and
   a transverse hanger member attached to and extending between substantially the midpoints of said semi-circular hanger members transverse to a line between the points at which said semi-circular hanger members are integrally attached to said ring member, and in the plane of said ring member in the non-use condition of said hanger, all of said members being made of a bendable resin material and the integral attachments of said semi-circular hanger members to said ring member and said transverse hanger member to said semi-circular hanger members are flexible and permit said members to hinge relative to each other, whereby said semi-circular hanger members can be pivoted upwardly out of the plane of said ring member and said transverse hanger member is looped upwardly for hooking over a laterally extending support member or hook on a stand, wall hook or the like for supporting the container in an inverted position.

2. A hanger as claimed in claim 1 in which said ring member has a cylindrical wall portion depending from the outer peripheral edge thereof for locating said hanger on the container.

3. A hanger as claimed in claim 1 further comprising breakaway connectors between said semi-circular hanger members and the inner peripheral edge of said ring member which are broken away when said semi-circular hanger members are pivoted out of the plane of said ring member.

4. A hanger as claimed in claim 3 in which said breakaway connectors are aligned with said transverse hanger member.

5. A hanger as claimed in claim 1 in which said transverse hanger member has projections on the surface thereof facing the bottom of the container when the hanger is on a container for spacing said transverse hanger member from the bottom of the container.

6. A hanger as claimed in claim 1 in which said ring member has at least two rib members thereon depending from the inner peripheral edge toward the bottom of the container when the hanger is on a container for spacing the ring member from the bottom of the container.

7. A hanger as claimed in claim 6 in which said rib members are adjacent the points at which said semi-circular hanger members are attached to said ring member.

8. A hanger as claimed in claim 1 in which said ring member has a rib member thereon extending around the inner periphery of said ring member and depending therefrom toward the bottom of the container when said hanger is on a container for spacing said ring member from the bottom of the container.

9. A hanger as claimed in claim 8 in which said ring member has a cylindrical wall portion depending from the outer peripheral edge thereof for locating said hanger on the container, and further has reinforcing ribs extending radially between said rib member and said cylindrical wall.

10. A container having a bottom and intended to be hung in an inverted position;
    a hanger for hanging the container in an inverted position and having:
    a ring member on the bottom of the container;
    a pair of semi-circular hanger members lying along and spaced from the inner peripheral edge of said ring member and in the plane of said ring member in the non-use condition of said hanger, and semi-circular hanger members having the ends integrally attached to the inner peripheral edge of said ring member at substantially diametrically opposite points of said ring member;
    a transverse hanger member attached to and extending between substantially the midpoints of said semi-circular hanger members transverse to a line between the points at which said semi-circular hanger members are integrally attached to said ring member, and in the plane of said ring member in the non-use condition of said hanger, all of said members being made of a bendable resin material and the integral attachments of said semi-circular hanger members to said ring member and said transverse hanger member to said semi-circular hanger members are flexible and permit said members to hinge relative to each other, whereby said semi-circular hanger members can be pivoted upwardly out of the plane of said ring member and said transverse hanger member is looped upwardly for hooking over a laterally extending support member or hook on a stand, wall hook or the like for supporting the container in an inverted position; and
    means for holding said hanger against the bottom of said container.

11. The combination as claimed in claim 10 in which said means for holding said hanger against the bottom of said container comprises a film of heat shrinkable synthetic resin heat shrunk around said container and extending over at least part of the width of said ring member.

12. The combination as claimed in claim 11 in which said film extends inwardly of said ring member past the inner peripheral edge thereof.

13. The combination as claimed in claim 10 in which said ring member has a cylindrical wall portion depending from the outer peripheral edge around the container.

14. The combination as claimed in claim 10 further comprising breakaway connectors between said semi-circular hanger members and the inner peripheral edge of said ring member which are broken away when said semi-circular hanger members are pivoted out of the plane of said ring member.

15. The combination as claimed in claim 14 in which said breakaway connectors are aligned with said transverse hanger member.

16. The combination as claimed in claim 10 in which said transverse hanger member has projections on the surface thereof extending toward the bottom of the container for spacing said transverse hanger member from the bottom of the container.

17. The combination as claimed in claim 10 in which said ring member has at least two rib members thereon depending from the inner peripheral edge toward the bottom of the container for spacing the ring member from the bottom of the container.

18. The combination as claimed in claim 17 in which said rib members are adjacent the points at which said semi-circular hanger members are attached to said ring member.

19. The combination as claimed in claim 10 in which said ring member has a rib member thereon extending around the inner periphery of said ring member and depending therefrom toward the bottom of the container for spacing said ring member from the bottom of the container.

20. The combination as claimed in claim 19 in which said ring member has a cylindrical wall portion depending from the outer peripheral edge around the container, and further has reinforcing ribs extending radially between said rib member and said cylindrical wall.

* * * * *